United States Patent [19]
Resch

[11] Patent Number: 5,006,529
[45] Date of Patent: Apr. 9, 1991

[54] SOAP COMPOSITIONS OF ENHANCED ANTIMICROBIAL EFFECTIVENESS

[75] Inventor: Carol M. Resch, Rutherford, N.J.

[73] Assignee: Lever Brothers Company, New York, N.Y.

[21] Appl. No.: 541,231

[22] Filed: Jun. 20, 1990

Related U.S. Application Data

[62] Division of Ser. No. 322,858, Mar. 14, 1989, Pat. No. 4,954,281, which is a division of Ser. No. 199,568, May 27, 1988, Pat. No. 4,832,861.

[51] Int. Cl.[5] .................... A01N 31/14; C11D 3/48; C11D 9/32; A61K 31/075

[52] U.S. Cl. .................... 514/721; 252/106; 252/107; 252/121; 252/134; 252/557; 252/DIG. 16; 514/706

[58] Field of Search .................... 252/106, , 107, 121, 252/134, 554, 557, DIG. 16; 514/721, 706

[56] References Cited

U.S. PATENT DOCUMENTS

| | | | |
|---|---|---|---|
| 3,625,903 | 12/1971 | Davies et al. | 252/107 |
| 3,969,259 | 7/1976 | Lages | 252/107 |
| 4,109,010 | 8/1978 | Sias | 514/494 |
| 4,111,844 | 9/1978 | Polony et al. | 252/106 |
| 4,115,294 | 9/1978 | Fearnley et al. | 252/106 |
| 4,235,733 | 11/1980 | Watanabe et al. | 252/107 |
| 4,282,110 | 8/1981 | Koike | 252/107 |
| 4,288,341 | 9/1981 | Hooper et al. | 252/107 |
| 4,326,978 | 4/1982 | Moesch | 252/107 |
| 4,339,462 | 7/1982 | Muntwyler et al. | 424/341 |
| 4,490,280 | 12/1984 | Joshi et al. | 252/368 |
| 4,543,204 | 9/1985 | Gervanio | 252/531 |
| 4,584,126 | 4/1986 | Joshi | 252/134 |
| 4,663,070 | 4/1987 | Dobrovolny et al. | 252/121 |
| 4,695,395 | 9/1987 | Caswell et al. | 252/121 |
| 4,714,563 | 12/1987 | Kajs et al. | 252/107 |

FOREIGN PATENT DOCUMENTS 2175005 11/1986 United Kingdom .

*Primary Examiner*—Josephine Barr
*Assistant Examiner*—Erin M. Harriman
*Attorney, Agent, or Firm*—Milton L. Honig

[57] ABSTRACT

A cleaning composition is disclosed comprising a mixture of soap, non-soap anionic surfactant and 2,4,4'-trichloro-2'-hydroxy diphenyl ether. Especially preferred surfactants are acyl isethionate and alkyl glycerol ether sulfonate salts. The ratio of fatty acid salt to surfactant ranges from 4:1 to 1:0.98.

5 Claims, No Drawings

SOAP COMPOSITIONS OF ENHANCED ANTIMICROBIAL EFFECTIVENESS

This is a divisional application of Ser. No. 322,858 filed Mar. 14, 1989, U.S. Pat. No. 4,954,281, which is a divisional of Ser. No. 199,568 filed May 27, 1988, now issued U.S. Pat. No. 4,832,861.

BACKGROUND OF THE INVENTION

1. Field of the Invention

The invention relates to soap compositions of enhanced antimicrobial effectiveness.

2. The Prior Art

Consumers are quite concerned with the elimination of body odor. This concern has provided a very large market for deodorant and antimicrobial soap bars.

Demand for such products began just prior to World War II with the introduction of Lifebuoy® soap containing phenolic actives. Advertising for this soap brought the term "B.O." into the common vocabulary.

About 1950, a further class of chemicals known as bacteriostats were introduced into soap bars. These chemicals control bacteria which cause sweat to break down into malodorous components. Over the years the most widely used actives were hexachlorophene; chlorhexidine; 3,4,4'-trichlorocarbanilide; 3,4',5 -tribromosalicylanilide; 4,4'-dichloro-3'-(trifluoromethyl) carbanilide; and 2,4,4'-trichloro-2'-hydroxy diphenyl ether.

Prior research into reducing the microbial count primarily focused upon the nature of the bacteriostat. Apparently little attention has been directed at the interaction of surfactants, e.g. soap or syndet, with that of the antimicrobial active agent. Of particular interest is the question of whether bars fashioned from significant amounts of non-soap surfactant have similar antimicrobial responses to that of soap. Furthermore, there has also remained the question of whether highly skin mild toilet bar formulations would interact well with bacteriostats.

Therefore, it is an object of the present invention to provide a cleaning composition, especially in the form of a toilet bar, which would have enhanced deodorant and antimicrobial activity.

A further object of this invention is to provide a cleaning composition, particularly a toilet bar, containing a bacteriostat that will not impair skin mildness or other physical properties of the composition.

SUMMARY OF THE INVENTION

A cleaning composition is herein disclosed comprising:

(i) a $C_{12}$–$C_{22}$ fatty acid salt;

(ii) a non-soap anionic surface active agent: and (iii) 2,4,4'-trichloro-2'-hydroxy diphenyl ether in an amount effective to reduce body odor, the ratio of fatty acid salt to surface active agent being from about 4:1 to 1:0.98.

Particularly useful are compositions in the form of toilet bars comprising (i) sodium salt of $C_{12}$–$C_{22}$ fatty acids; (ii) $C_8$–$C_{22}$ acyl isethionate or alkyl glycerol ether sulfonate salts; and (iii) antimicrobial agent. Preferably, the relative amount of fatty acid salt to surface active agent ranges from 2.5:1 to 1.5:1.

DETAILED DESCRIPTION OF THE INVENTION

According to this invention, it has been found that improved antimicrobial activity can be obtained with a combination of soap and a non-soap anionic surface active agent when using 2,4,4'-trichloro-2'-hydroxy diphenyl ether. Combination of these surfactants provides a much more active base than either of the two materials separately. It is important that the amounts of soap and non-soap syndet be held within narrow ranges to achieve this result.

An important component of the formulation, as above noted, is 2,4,4'-trichloro-2'-hydroxy diphenyl ether (commercially available as DP-300® from the Ciba-Geigy Corporation). Effective amounts of this material range anywhere from 0.05% up to 2%, preferably between 0.10 and 1%, optimally between 0.15 and 0.6%. Within the formulations of this invention, the bacteriostat is particularly effective against the gram negative bacilli.

The compositions of this invention must contain a certain amount of "soap" which herein is meant to be alkali metal salts of aliphatic alkane- or alkene monocarboxylic acids, more generally known as $C_{12}$–$C_{22}$ alkyl fatty acids. Sodium and potassium salts are preferable. Alkanolammonium salts such as those formed from triethanolamine have certain deficiencies which are not considered useful for this invention and are therefore outside its scope. A preferred soap is a mixture of about 15% to about 20% coconut oil and about 80% to about 85% tallow.

The soaps may contain unsaturation in accordance with commercially acceptable standards. Excessive unsaturation is normally avoided.

Total soap content of the invention compositions must be greater than 25 wt. %. Usually, from about 30% to 70% of the composition is soap. Preferably, the concentration of this component ranges from about 35% to 60%, more preferably 45% to 55%.

Soap formulations encompassed by this invention may either be in liquid, gel or toilet bar form. When in bar form, the bar should be opaque rather than translucent or transparent, the latter types being deficient in physical and user properties.

A third critical component of compositions under this invention is that of a non-soap anionic surface active agent, or syndet. Particularly suitable syndets for this invention are the $C_8$–$C_{22}$ acyl isethionates. These esters may be prepared by the reaction between alkali metal isethionate and mixed aliphatic fatty acids having from 8 to 22 carbon atoms and an Iodine Value of less than 20. At least 75% of the mixed fatty acids should preferably have from 12 to 18 carbon atoms and up to 25% should have from 8 to 10 carbon atoms.

Another suitable syndet is that of alkyl glycerol ether sulfonate. Alkyl chains for this surfactant are from $C_8$ to $C_{22}$, preferably $C_{10}$ to $C_{18}$.

The ratio of fatty acid salt to the non-soap surface active agent is highly important. It may range from about 4:1 to 1:0.98, preferably from about 2.5:1 to 1.5:1, optimally about 2:1.

Free fatty acids of 8–22 carbons are desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8–18, preferably 10–16, in an amount up to 25% by weight of the composition. Skin feel and creaminess enhancers, the most important of which is stearic acid, are also desirably present in these compositions. Levels of stearic acid can range from 1% up to 40%, preferably between 5% and 25%.

Other performance chemicals and adjuvants may be needed with these compositions The amount of these chemicals and adjuvants may range from about 1% to about 40% by weight of the total composition. Illustrative of these materials are perfumes, pigments or dyes, preservatives, electrolyte salts, water and mixtures thereof.

The following examples will more fully illustrate the embodiments of this invention. All parts, percentages and proportions referred to herein and in the appended claims are by weight of the total composition unless otherwise stated.

EXAMPLE 1

Herein is described results of Skin Disc Substantivity Tests involving a number of toilet bars whose compositions are outlined in Table I. Bar A comprised soap:cocoyl isethionate in a ratio 2.3:1, representing a formula of the invention. Bars B and C are typical commercial all soap bars, except the former was compounded with 0.25% DP-300. Bar D contained sodium cocoyl isethionate and soap (ratio 4.4:1) with 0.25% DP-300®. Bars E and F were identical with that of Bars D and A but had no antibacterial agent.

TABLE I

Sample Toilet Bar DP-300 ® Compositions

| Sample Bar | Commercial Type Bar | Soap:Acyl Isethionate Ratio | % DP-300 |
|---|---|---|---|
| A | Lever 2000 ® | 2.3:1 | 0.25 |
| B | Lifebuoy ® | all soap | 0.25 |
| C | Lux ® | all soap | — |
| D | Dove ® | 1:4.4 | 0.25 |
| E | Dove ® | 1:4.4 | — |
| F | Lever 2000 ® | 2.3:1 | — |

Method

In Vitro Skin Disc Substantivity Test

Six calf skin discs per test were soaked in deionized water for 15 minutes. Soap slurries were prepared by dissolving 8 grams of soap in 100 ml deionized water at 45° C. The hydrated 6 mm diameter discs were placed in the test soap slurries at room temperature for 15 minutes, rinsed under warm running tap water for 15 minutes, and excess water removed with paper toweling. The discs were then placed on AATCC Bacteriostasis Agar seeded with *Staphylococcus aureus* ATCC #6538, *Escherichia coli* ATCC #10538, *Salmonella typhimurium* ATCC #14028, *Staphylococcus epidermidis* ATCC #12228 or *Klebsiella pneumoniae* ATCC #4352. The discs were removed after 30 minutes and the plates incubated at 37° C. for 18 to 24 hours. Bacterial growth at the sites where the discs had been placed was estimated on a 0 to 4 scale.

The grading system was as follows:

0—No activity
1—Slight activity
2—Moderate activity
3—Strong activity

4—Complete inhibition

TABLE II

Skin Disc Substantivity Test Results on DP-300 ® Compositions

| Sample Bar | *Staphylococcus aureus* | *Escherichia coli* | *Salmonella typhimurium* | *Staphylococcus epidermidis* | *Klebsiella pneumoniae* |
|---|---|---|---|---|---|
| A | 4/6** | 1.2/0 | 1.8/0 | 3.5/2.7*** | 4/0.7 |
| B | 3.6/5.3** | 0.9/0 | 2.0/0 | — | — |
| C | 2.4/0 | 0 | 0 | 0 | 0 |
| D | 3.4/5.3* | 0.6/0 | 1.0/0 | — | — |
| E | 0 | 0 | 0 | 0 | 0 |
| F | 0 | 0 | 0 | 0 | 0 |

*with 2 mm Secondary Partial Inhibition Zone
**with 3.0 mm Secondary Partial Inhibition Zone
***with 4.0 mm Secondary Partial Inhibition Zone From Table II, it is sen that Bar A had better bacteriostat activity than any of the other bars tested. Apparently, there is some unexpected interaction between DP-300 ® and a soap/acyl isethionate formula of ratio 2.3:1 relative to that obtainable with either pure soap or the 1:4.4 ratio.

TABLE III

Sample Toilet Bar TCC Compositions

| Sample Bar | Commercial Type Bar | Soap:Acyl Isethionate Ratio | % TCC* |
|---|---|---|---|
| G | Lever 2000 ® | 2.3:1 | 0.85 |
| H | Dove ® | 1:4.4 | 0.85 |
| I | Lux ® | all soap | 0.85 |
| J | Lever 2000 ® | 2.3:1 | — |
| K | Dove ® | 1:4.4 | — |
| L | Lux ® | all soap | — |

*3,4,4'-trichlorocarbanilide

TABLE IV

Skin Disc Substantivity Test Results on TCC Compositions

| Sample Bar | *Staphylococcus aureus* | *Staphylococcus epidermidis* | *Klebsiella pneumoniae* |
|---|---|---|---|
| G | 2.2/0 | 2.8/0 | 0 |
| H | 1.3/0 | 1.3/0 | 0 |
| I | 1.7/0 | 2.3/0 | 0 |
| J | 0 | 0 | 0 |
| K | 0 | 0 | 0 |
| L | 0 | 0 | 0 |

From Table IV, is it apparent that the Lever 2000 ® base formula of soap/acyl isethionate interacts much more effectively with TCC (Triclocarban) than does either an all-soap or Dove ® type surfactant stock. In general, the TCC is less effective than DP-300 ®.

EXAMPLE 2

Illustrative of compositions within the present invention are the formulations appearing in Tables V and VI.

TABLE V

| Components | Weight % |
|---|---|
| Sodium Soap (82/18)* | 50.73 |
| Sodium cocoyl isethionate | 21.74 |
| Water | 11.45 |
| Stearic Acid | 6.98 |
| Sodium isethionate | 5.00 |
| Miscellaneous (perfume, colorants, preservatives) | 2.10 |
| Coconut fatty acid | 1.32 |
| Sodium chloride | 0.43 |
| DP-300 ® | 0.25 |

*Tallow to coconut oil ratio

TABLE VI

| Components | Weight % |
|---|---|
| Sodium Soap (60/40)* | 45.72 |
| Sodium alkyl glyceryl ether sulfonate | 16.37 |
| Stearic acid | 25.38 |
| Water | 3.70 |
| Miscellaneous (perfume, colorants, preservatives) | 3.44 |
| Sodium chloride | 3.04 |
| Miscellaneous (perfume, colorants, preservatives) | 2.10 |
| DP-300 ® | 0.25 |

*Tallow to coconut oil ratio

The foregoing description and examples illustrate selected embodiments of the present invention and in light thereof various modifications will be suggested to one skilled in the art, all of which are within the spirit and purview of this invention.

What is claimed is:

1. A method for controlling the growth of bacteria on the skin comprising applying to the skin water and a toilet bar whose composition comprises:

(i) from 30 to 70% of a $C_{12}$–$C_{22}$ fatty acid salt;

(ii) a non-soap anionic surface active agent which is a $C_{10}$–$C_{22}$ acyl isethionate salt;

(iii) from 1 to 40% of $C_{12}$–$C_{18}$ free fatty acid;

(iv) from 0.5 to 15% of sodium isethionate; and (v) from 0.1 to 2% of 2,4,4'-trichloro-2'-hydroxy diphenyl ether in an amount effective to reduce body odor, the ratio of fatty acid salt to surface active agent being from 2.5:1 to 1.5:1.

2. A method according to claim 1 wherein the fatty acid salt to surface active agent ratio is about 2:1.

3. A method according to claim 1 wherein the bar is opaque.

4. A method according to claim 1 wherein the $C_{12}$–$C_{22}$ fatty acid salt is present in an amount from 35 to 60%.

5. A method according to claim 1 wherein the composition further comprises adjunct ingredients selected from the group consisting of Perfumes, colorants, preservatives, electrolyte salts, water and mixtures thereof.

* * * * *